United States Patent
Burd et al.

[11] Patent Number: 5,939,331
[45] Date of Patent: *Aug. 17, 1999

[54] RED BLOOD CELL SEPARATION MEANS FOR SPECIFIC BINDING ASSAYS

[75] Inventors: John Burd; Steven Miller; Gerald Rowley; Allan Pronovost, all of San Diego, Calif.

[73] Assignee: Quidel Corporation, San Diego, Calif.

[ * ] Notice: This patent is subject to a terminal disclaimer.

[21] Appl. No.: 08/066,410

[22] Filed: May 21, 1993

Related U.S. Application Data

[63] Continuation of application No. 07/847,487, Mar. 10, 1992, abandoned.

[51] Int. Cl.$^6$ .................................................. G01N 33/53
[52] U.S. Cl. ..................... 436/518; 435/7.9; 435/7.92; 435/7.93; 435/7.94; 435/7.95; 435/962; 435/969; 435/970; 436/527; 436/531; 436/535; 436/825
[58] Field of Search ............................ 435/7.9, 7.92–7.95, 435/805, 962, 969, 970; 436/518, 527–535, 169–170, 810, 825; 422/56–58, 101

[56] References Cited

U.S. PATENT DOCUMENTS

| | | | |
|---|---|---|---|
| 3,552,928 | 1/1971 | Fetter | 435/805 X |
| 3,992,158 | 11/1976 | Przybylowicz et al. | 435/805 X |
| 4,258,001 | 3/1981 | Pierce et al. | 422/56 |
| 4,366,241 | 12/1982 | Tom et al. | 435/7.92 X |
| 4,426,451 | 1/1984 | Columbus | 436/518 |
| 4,477,575 | 10/1984 | Vogel et al. | 436/170 |
| 4,548,905 | 10/1985 | Wu | 422/56 X |
| 4,594,327 | 6/1986 | Zuk | 436/514 |
| 4,678,757 | 7/1987 | Rapkin et al. | 422/56 X |
| 4,774,192 | 9/1988 | Terminiello et al. | 436/530 |
| 4,839,296 | 6/1989 | Kennedy | 422/57 X |
| 4,861,711 | 8/1989 | Friesen et al. | 435/7.92 |
| 4,916,056 | 4/1990 | Brown, III et al. | 422/57 X |
| 4,943,522 | 7/1990 | Eisinger et al. | 422/58 X |
| 4,956,301 | 9/1990 | Ismail et al. | 436/87 |
| 4,959,324 | 9/1990 | Ramel et al. | 422/58 X |
| 4,987,085 | 1/1991 | Allen et al. | 422/58 X |
| 5,075,078 | 12/1991 | Oslkowicz et al. | 422/56 |
| 5,079,142 | 1/1992 | Coleman et al. | 435/7.92 |
| 5,082,626 | 1/1992 | Grage, Jr. | 422/56 |
| 5,116,576 | 5/1992 | Stanley | 422/58 X |
| 5,120,643 | 6/1992 | Ching et al. | 435/7.92 |
| 5,135,872 | 8/1992 | Pouletty et al. | 436/180 |
| 5,166,051 | 11/1992 | Killeen et al. | 435/7.1 |
| 5,308,775 | 5/1994 | Donovan et al. | 436/518 |
| 5,558,834 | 9/1996 | Chu et al. | 422/55 |
| 5,559,041 | 9/1996 | Kang et al. | |

FOREIGN PATENT DOCUMENTS

| | | | |
|---|---|---|---|
| 0287731 | 10/1988 | European Pat. Off. | |
| 2204398 | 11/1988 | United Kingdom | 422/56 |

*Primary Examiner*—Carol A. Spiegel
*Attorney, Agent, or Firm*—Morrison & Foerster LLP

[57] ABSTRACT

A method and device for detecting the presence, absence or amount of an analyte in a whole blood sample is disclosed. The device comprises four zones, a sample receiving zone, a labeling zone, a capture zone and an absorbent zone. The sample receiving zone contains an irreversibly immobilized reagent that allows for removal of substantially all red blood cells from the whole blood sample. Flow through the device is via capillary migration and all of the dissolved or dispersed components in the sample flow at substantially equal rates and with relatively unimpaired flow through the device. The method involves the use of the device for detection of analyte in a whole blood sample.

11 Claims, 1 Drawing Sheet

RED BLOOD CELL SEPARATION MEANS FOR SPECIFIC BINDING ASSAYS

This application is a continuation of application Ser. No. 07/847,487, filed Mar. 10, 1992, and now abandoned.

TECHNICAL FIELD

The invention relates to immunological and related assay methods and apparatus, especially those used in blood testing.

BACKGROUND OF THE INVENTION

The literature on various forms of diagnostic test methods including specific binding assays, especially immunoassays, is extensive and commercial products are numerous. A large number of simplified and conveniently packaged assays are currently available. Nonetheless, there remains a need for assay devices which are easy to use and interpret.

Whole blood samples may obscure the reading of test results due to turbidity and color. In order to solve this problem, previous investigators have described devices which both separate out the Red Blood Cells (RBCs) and analyze the resultant plasma or serum for a particular dissolved component. EPO Publication No. 287731 to Maddox describes a dry test device comprising an absorbent reagent zone containing a chemical assay or immunoassay and an analyte target having a polysaccharide material that can limit the passage of RBCs or hold the RBCs on or near the surface of the absorbent reagent zone. A one-step procedure, employing simultaneous separation from whole blood with testing for a desired component is described in U.S. Pat. No. 4,678,757 to Rapkin et al. Blood is applied to the surface of a carbohydrate-treated carrier. The fluid portion migrates away from the point of contact and the cellular components remain in close proximity to the point of contact. If the carrier is further treated with a reagent employed to detect a component, a color will appear in the fluid. U.S. Pat. No. 3,552,928 to Fetter describes a means for separation of whole blood into a colorless fluid and a red cell or residue component. The whole blood is contacted with a separative reagent (a water-soluble, nonvolatile amino acid), the residue is removed and the remaining fluid can be contacted with a test reagent. Both reagents may be contained on a single matrix (i.e. bibulous filter paper), however, the matrix must allow the colorless fluid to flow from the separating reagent to the test reagent. U.S. Pat. No. 4,594,327 to Zuk describes a procedure whereby blood is first treated with a red blood cell precipitant, such as an antibody, lectin or certain polymeric amino acids, and then passed into an "immunochromatograph." The red blood cells remain at the liquid/air interface.

U.S. Pat. No. 4,943,522 to Eisinger et al. describes methods and apparatus for conducting specific binding pair assays, such as immunoassays. A porous membrane capable of non-bibulous lateral flow is used as assay substrate. A member of the binding pair is affixed in an indicator zone defined in the substrate. The sample is applied at a position distant from the indicator zone and permitted to flow laterally through the zone. Analyte in the sample is complexed by the affixed specific binding member and detected.

All patents, patent applications, and publications mentioned herein, whether supra or infra, are hereby incorporated by reference.

DISCLOSURE OF THE INVENTION

The invention provides a method to prepare a blood fluid sample that is substantially free of red blood cells (RBCs). This method comprises flowing a whole blood sample through a bibulous or non-bibulous solid support that contains a reagent, such as antibodies or their immunologically reactive fragments, directed against RBCs or their components. The portion of the blood fluid sample which is substantially free of RBCs is recovered from the solid support.

In another aspect, the invention provides a method and device for determining the presence or absence or the amount of analyte using a specific binding assay. The device comprises a lateral flow membrane which has a sample application zone that contains a reagent such as antibody directed to RBCs to receive the whole blood sample and capture the red blood cells to result in a substantially RBC-free fluid, and an extension of the lateral flow membrane for analysis of the remaining fluid. The extension need not be composed of solid support matrix identical to that of the sample application zone. In one embodiment, this extension comprises a label zone that contains a label capable of specifically binding to or competing with the analyte in the assay, a capture zone comprising a matrix containing a reagent capable of binding the label or analyte bound to label, and an absorbent pad for absorbing the remainder of the sample.

In an alternate embodiment of the foregoing device, the label zone itself rather than the sample application zone contains the antibody that will capture the red blood cells.

Another aspect of the invention is directed to a method to determine the presence or absence of analyte in a sample. The method comprises contacting the sample with a solid support matrix containing at least one reagent such as an antibody to retain the RBCs in the sample in the matrix, flowing the resultant RBC-free fluid onto a label pad where the analyte in the sample is bound to label, or where label competitive for a specific binding agent is mobilized into the liquid, passing the label into a capture zone and observing the binding of label in the capture zone as a direct or inverse measure of the presence or absence or amount of analyte.

MODES FOR CARRYING OUT THE INVENTION

Figure 1:
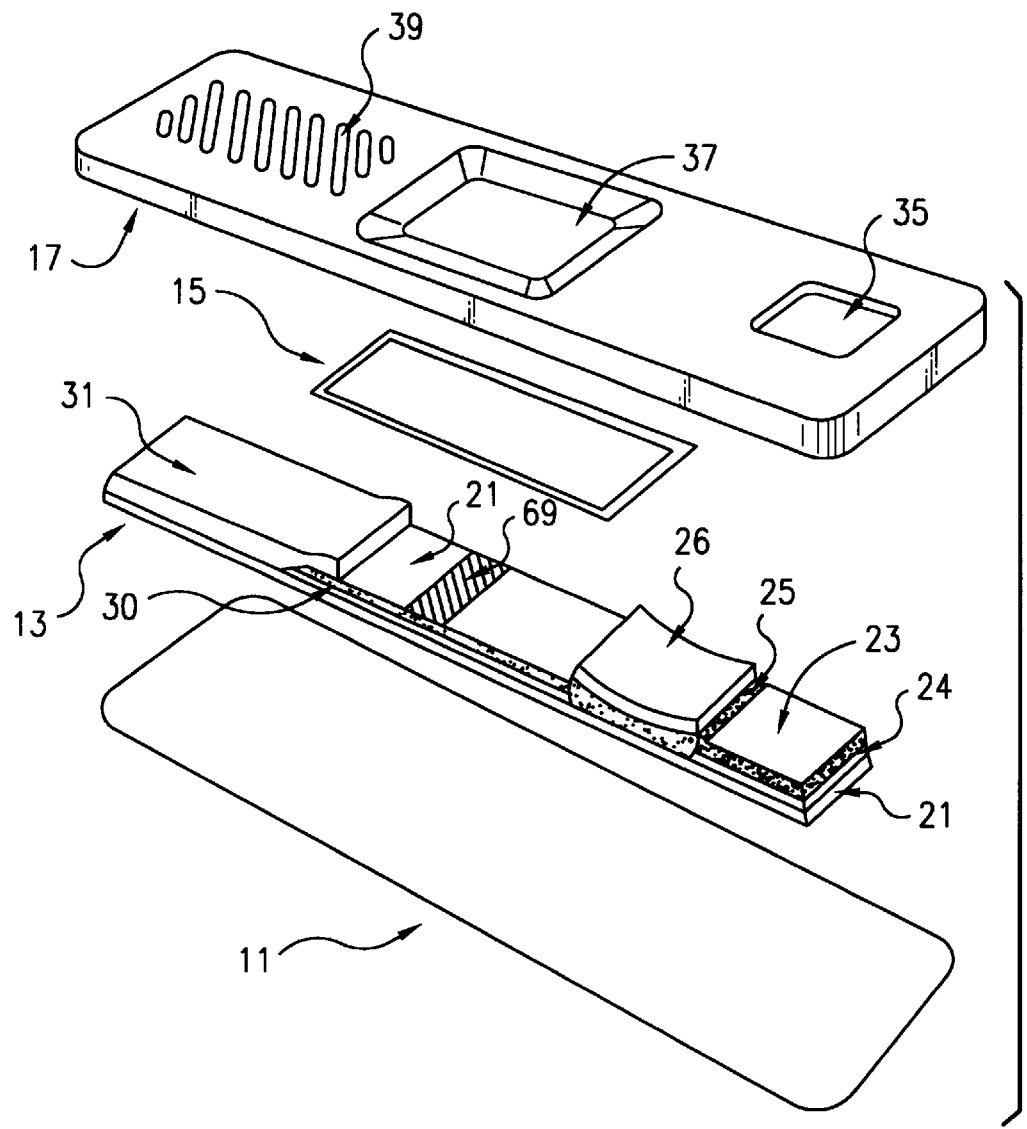
FIG. 1 is an exploded view of the preferred embodiment of the invention.

The invention is useful for a wide variety of assay strategies wherein a blood fluid sample that is substantially free of red blood cells (RBCs) is required.

All of the embodiments of the method of the invention employ a solid support matrix containing a specific binding reagent for red blood cells through which a whole blood sample can be passed. In passing the whole blood sample through this solid support, the red blood cells are removed and the remaining fluid, free of RBCs, is recovered, either directly or by passage through an extension of the solid support into regions wherein additional reagents are supplied. The fluid is thus made susceptible to determination of a particular analyte suspected of being contained therein.

Solid Supports

An essential feature of the method of the invention is the employment of a solid support matrix, such as a membrane capable of lateral flow, that contains a capture reagent for red blood cells. The membranes employed may allow for either bibulous or non-bibulous flow. By "non-bibulous" flow is meant liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components. "Bibulous" materials include paper, nitrocellulose, nylon and the like, which have the capability to effect a chromatographic separation of the contained materials. These materials can be made non-bibulous by use of a suitable coating procedure.

An example of membrane material in which capillary, non-bibulous flow occurs is spunlaced fabric manufactured to contain 100% acrylic fiber or varying fiber blends. The fabric typically has a non-woven structure made of hydraulically interlaced fibers with no chemical or thermal bonding. One example of this material is "SONTARA" (100% spun-laced acrylic fiber, Dupont, Wilmington, Del., U.S.A.), manufactured by Dupont, Wilmington, Del., U.S.A.

Another example of membrane material in which capillary, non-bibulous flow occurs is the high density or ultra high molecular weight polyethylene sheet material manufactured by Porex Technologies Corp. of Fairburn, Ga., U.S.A. This membrane has an open pore structure with a typical density, at 40% void volume, of 0.57 gm/cc and an average pore diameter of 1 to 250 micrometers, the average generally being from 3 to 100 micrometers. The optimum pore diameter for the membrane for use in the invention is about 10 to about 50 $\mu$m. The membranes are from about 0.1 mm to 5 mm in thickness. The membrane may be backed with a generally water impervious layer to accommodate lateral flow, or may be totally free standing. While membranes made of polyethylene have been found to be highly satisfactory, lateral flow, non-bibulous membranes formed of other olefins or other thermoplastic materials, e.g., polyvinyl chloride, polyvinyl acetate, copolymers of vinyl acetate and vinyl chloride polyamide, polycarbonate, polystyrene, etc. can be used. Membranes formed by the classical phase inversion process may also be used.

Thus, the non-bibulous membranes, in general, will have a pore size of about 1–100 $\mu$m, preferably about 5–20 $\mu$m; will be constructed or an inert material; and will be less than 5 mm thick. They can conduct lateral flow, but isotropic flow may also be employed. While applicants believe this non-bibulous flow to be caused, at least in part, by capillary action, they are not bound by any particular theory to explain the characteristic nature of this flow.

Solid supports capable of conducting non-bibulous flow can also be obtained by treating bibulous solid supports with coatings which interfere with the attractive forces exerted by the bibulous materials. Thus, materials which in the their untreated state are bibulous, such as paper, nitrocellulose and nylon can be converted to a non-bibulous flow characteristic by treating the native material with suitable blocking agents such as methylated bovine serum albumin and the like. Methods to convert bibulous solid supports to supports with non-bibulous flow characteristics are described in detail in U.S. Ser. No. 639,967, filed Jan. 11, 1991, assigned to the same assignee and incorporated herein by reference.

Bibulous material, however, can be converted to those which exhibit nonbibulous flow characteristics by the application of blocking agents, in particular, certain detergents and proteins, which obscure the interactive forces that account for the bibulous nature of the supports per se. Thus, nonbibulous materials include those which are intrinsically capable of conducting nonbibulous flow, such as porous polyethylene sheets or other inert materials or can be comprised of bibulous materials which have been blocked. Preferred blocking agents include bovine serum albumin, either per se or in methethylated or succinylated form, whole animal sera, such as horse serum or fetal calf serum, and other blood proteins. Other protein blocking agents include casein and non-fat dry milk.

Detergent based blocking agents can also be used. The types of detergents which are appropriate are selected from nonionic, cationic, anionic and amphoteric forms, and the selection is based on the nature of the membrane being blocked. Considerations which govern the selection of the appropriate detergent blocking agent are well understood in the art. It is preferred to use detergents in combination with protein-based blocking agents. Suitable detergents which can be used either alone or in admixture with the protein blocking agents include polyoxyethylene sorbitan alcohol detergents (i.e., the Tween series), polyoxyethylene alcohols such as Nonidet P-40 or polyoxyethylene ethers such as Triton X-100. The selection of blocking agent and formulation of the blocking composition is important, as the blocking must be sufficient to effect non-bibulous flow, but the modified surface must not interfere with analyte-label-capture interaction.

One improvement which is the basis for the present invention is the use of, in the assay devices herein or in assay devices which utilize nonbibulous lateral flow in general, matrices or supports that are formed by the conversion of membranes or other supports with bibulous characteristics to nonbibulous membranes or supports. This is effected through application of blocking solutions. While intrinsically nonbibulous supports, such as the polyethylene sheet material manufactured by Porex Technologies Corporation (described in the above-referenced U.S. Pat. No. 4,943,522), can be employed in lateral flow assays, the use of converted microporous bibulous supports is preferred and has some advantages, such as more efficient immobilization of a capture binding reagent and resulting increased sensitivity, improved lateral flow and enhanced speed of detection.

To convert a bibulous support such as paper or nitrocellulose to a support capable of effecting nonbibulous lateral flow, the original support is treated with a solution of the blocking agent in an effective concentration to dispose of unwanted reactivities at the surface. In general, this treatment is conducted with a blocking solution, such as a protein solution of 1–20 mg/ml protein at approximately room temperature for several minutes—several hours. The resulting coated material is then permanently absorbed to the surface by air-drying, by lyophilization or other drying methods.

The solid supports used in the method of the invention may also conduct bibulous flow.

Red Blood Cell Binding Reagents

The reagent which is capable of binding red blood cells that is contained in the solid support matrix, such as those described above, is typically and most preferably an antibody, polyclonal or monoclonal, which is specific for red blood cells. Such antibodies can be prepared using standard immunization protocols by administering RBC from a foreign species to an antibody-producing host. The resulting antisera can be used per se in the solid support matrices of the invention or the immunoglobulins from the antiserum can be purified using standard techniques to obtain an immunoglobulin fraction. The immunoglobulin may be further purified using affinity chromatography with the RBC antigen as affinity ligand. Monoclonal antibodies may also be prepared from the lymphocytes or spleen of the immunized subjects. Antibody fragments, Fab, Fab', and F(ab')$_2$ of polyclonal or monoclonal antibodies can also be employed. Alternatively, other reagents which are known to bind red blood cells, such as lectins or polymeric amino acids, e.g., polylysine and polyarginine, may also be used.

The RBC-binding reagent is then immobilized on the solid support matrix using standard techniques, mostly dependent on the nature of the matrix chosen. For relatively inert matrices, the matrix is treated with a solution or dispersion of the binding reagent and the solvent is removed by drying or lyophilization, resulting in passive adherence to the support. Alternatively, derivatized supports may be used to effect covalent bonding of the support to the reagent.

Conduct of the Invention Method

In the method of the invention, the whole blood sample is applied to the solid support matrix containing the RBC-binding reagent and allowed to pass through the matrix, exiting as a substantially RBC-free fluid which can then be used directly for analysis. In one embodiment of this method, the whole blood is simply passed through the solid support matrix which is managed in a manner analogous to a simple filter and recovered as a fluid which can then be utilized as desired.

Alternatively, and preferably, the solid support matrix is extended by additional solid support capable of conducting bibulous and/or nonbibulous flow so that the separation of the RBC from the remaining fluid and the steps in the analysis are conducted in a single device, such as that described below. In this embodiment, the solid support matrix containing RBC-binding reagent is in fluid communication with additional solid support matrix which may contain additional elements useful in analysis. For example, the extended solid support matrix through which the RBC-free fluid exits may contain a capture zone capable of specifically capturing a desired analyte. The analyte captured in the capture zone can then be detected by any suitable means such as treating the capture zone with developing and detecting reagents containing label. Alternatively, as described below, the label may be supplied by a label zone included in the extended solid support. A large number of specific protocols involving immunoassays or specific binding assays on solid supports have been described in the art. Any of these protocols may properly be employed with respect to the fluid exiting the separation solid support matrix that retains the RBC.

It should be emphasized that the extended solid support matrix into which the RBC-free fluid exits need not be comprised of the same material as that in which the RBC-binding reagent is contained. Thus, in addition to an embodiment wherein, for example, the RBC-binding reagent is contained at a defined portion of a single solid support matrix, or an ABC removal zone in a single solid support, the RBC removal zone may be supplied as a separate "RBC removal pad" and positioned contiguous with additional fluid-conducting matrix support comprised of the same or different polymeric construction.

Suitable Analytes

Suitable analytes to which some embodiments of the method of the invention can be applied are any for which a specific binding partner or competitor can be found. In general, most analytes of medical and biological significance can find specific binding partners in antibodies prepared against them or fragments of these antibodies; similarly, in most instances, either additional analyte itself or an immunologically cross-reactive analog may be employed to prepare label, and thus may serve as a suitable competitor. However, as is well known, specific binding interactions are not limited to antigen/antibody pairs, but may also include receptors and their ligands, enzymes and their substrates, polynucleotides and oligonucleotides, and the like.

Thus, suitable binding pairs for use in accordance with the invention include, but are not limited to the following types of interacting components: antigen/antibody; antibody/hapten; antibody/cell or cell fragment; RNA/DNA probes; receptor/receptor ligands; enzyme/substrate; enzyme/inhibitor and lectin/carbohydrate.

Suitable analytes include soluble analytes such as hormones, enzymes, lipoproteins, bacterial or viral antigens, immunoglobulins, lymphokines, cytokines, drugs, soluble cancer antigens, and the like. These analytes include various proteins such as protamines, histones, phosphorylated proteins, nucleoproteins, and so forth such as for example, transcortin, erythropoietin, transferrin, various globulins, thyroxine-binding globulin, the immunoglobulins of various subclasses A, G, D, E, and M, various complement factors, blood clotting factors such as fibrinogen, Factor VIII, tissue thromboplastin, and thrombin.

Also included are hormones such as insulin, glucagon, relaxin, thyrotropin, somatotropin, gonadotropin, follicle-stimulating hormone, gastrin, bradykinin, vasopressin, and various releasing factors. A wide range of antigenic polysaccharides, lipopolysaccharides, lipoproteins, proteoglycans and glycoproteins can also be determined such as those from Chlamydia, *Neisseria gonorrheae, Pasteurella pestis, Shigella dysentereae*, and certain fungi such as Mycosporum and Aspergillus. Yet another major group comprises oligonucleotide sequences which react specifically with other oligonucleotides or protein targets. Extensive lists and discussions of soluble analytes determinable in the method of the invention are found in U.S. Pat. No. 4,943,522, which is herein incorporated by reference in its entirety.

Assay Strategies

As is well known to those of skill in the art, a wide variety of possible assay strategies is available for determinations that can be performed on the RBC-free fluid, depending primarily on the nature of the analyte and the availability of suitable reagents for use in the assay. The experimental design protocol of the assays may therefore be varied as is generally known for assays based on specific binding. Such assays may include enzyme, fluorescence, chemiluminescence or other directly read visible labels. In particular, most protocols of immunoassay can be used to analyze the fluid free of RBCs prepared by the invention method.

One particularly preferred set of embodiments employs the fluid free of RBCs as it passes from the solid support containing the binding reagent into an extension of the same support or an extension composed of a different material comprising the solid support into which the RBC-free fluid can flow directly. Thus, in particularly preferred embodiments of the method of the invention, the solid support containing the RBC-binding reagent is contiguous with an extended solid support containing the reagents and reading zones suitable for the subsequent assay. The extended solid support may contain defined regions such as labeling zones, capture zones, absorbent zones and the like to comport with the design of the assay.

For example, where the analyte itself provides a visible label or where a visible label may be directly associated with the analyte prior to its introduction into the assay device, direct capture of now-visible analyte may be carried out in a capture zone on the extended region of the solid support using a capture reagent specific for the analyte. Most typically, however, assays in accordance with the present invention are directed to the detection of analytes which do not contain visible label or do not readily permit direct association of the visible label. For determination of the presence of such analytes, the assays may be carried out pursuant to one of the following strategies; coupling the visible label to a moiety that binds specifically to analyte; coupling the visible label to a moiety which binds an intermediary agent birding the analyte; or coupling the visible label to a moiety which competes with analyte for a capture reagent in a capture zone. Depending on the nature of the analyte, this last competitive assay protocol may also be suitable.

Thus, for preparation of an analyte-binding label, the visible label may be coupled to a binding partner that binds the analyte specifically. For example, if the analyte is an antigen, an antibody specific for this antigen (or immunologically reactive fragments of the antibody, such as $F(ab')_2$, Fab or Fab') would be a suitable carrier for the label moiety. These visible label-containing specific binding moieties then form complexes with any analyte in the sample either prior to introduction of the entire sample into the test device, as the sample passes through a labeling zone, or after the analyte is captured. For the first two approaches analyte/label complexes (as well as any unbound materials) can be carried into a capture zone by the liquid flow. When the complexes reach the capture zone, a capture reagent specific for analyte (such as an antibody or fragment thereof as set forth above) retains those coupled conjugates to which analyte has been bound; label which is not associated with analyte is not retained.

For those embodiments that employ a capture reagent and label that are both specific for analyte, it is preferred to use an excess of label so as to assure that all analyte in a sample is labeled prior to its introduction into the capture zone since any uncomplexed label is readily removed by washing. When both the label and the capture reagent are specific for the analyte, it may be necessary to select label and capture agent directed to different, non-overlapping binding sites on the analyte. For example, when the analyte is a polypeptide, the label and the capture reagent may suitably each comprise monoclonal antibodies immunospecific for different, non-overlapping epitopes of the polypeptide.

Other detection methods involve use of a labeled secondary reagent to detect the presence of a bound analyte (or binding partner therefor). Thus, for example, the presence of bound antibodies which are themselves analytes or that are specific binding agents to analytes in a detection zone could be evaluated using labeled anti-immunoglobulin antibodies, protein A or protein G. A particular advantage in the use of indirect detection methods is that a single labeled preparation of, e.g., anti-IgG antibodies could be used to detect a wide variety of different bound analyte/IgG complexes.

Competitive approaches employ a competing moiety which has at least one significant assay-related property in common with the analyte. For example, in the competitive binding approach, the visible label is coupled to a moiety which is competitive with analyte for a capture reagent in a detection or capture zone; most typically, labeled forms of the analyte itself are used as competitor. Both the analyte from the sample and the competitor bound to the label are then carried into a detection zone. While analyte and its competitor both react with the capture reagent (which most typically is specifically reactive with both analyte and its competitor), the unlabeled analyte is able to reduce the quantity of competitor-conjugated visible label that is retained in the detection zone. This reduction in retention of the visible label becomes a measure of the analyte in the sample.

Design of a Preferred Device

FIG. 1 is an exploded view of one embodiment of the device of the invention. The four basic layers of the device are as follows: the bottom cover 11, the test strip 13, the window 15 and the top cover 17.

The mylar base sheet 21 serves as an impermeable backing for the solid support portions that permit liquid flow. The sheet may be of any shape and of almost any size which may conveniently be handled. However, the sheet is preferably between about 3 and 11 mm wide by between about 50 and 150 mm long and between about 0.01 and 1 mm thick, more preferably the sheet is 9 mm wide by 90 mm long and 0.1 mm thick.

The exemplified test strip 13 comprises four distinct regions, a sample zone 23, a label zone 26, a nitrocellulose section 27 with capture zone 29, and an absorbent zone 31. Further, the test strip is contained in bottom cover 11 that is impervious to liquids and is made of a thermoplastic material such as polyvinyl chloride, polyvinyl acetate, copolymers of vinyl acetate and vinyl chloride polyamide, polycarbonate and polystyrene, and is preferably between about ⅝ and 1 inch wide and between about 3 and 4 inches long and between about 0.08 and 0.10 inches thick. More preferably the bottom cover is 0.45 inches wide and 3.06 inches long and 0.09 inches thick.

The sample zone 23 is typically constructed of a non-bibulous matrix such as "SONTARA" or "POREX" (high density or ultra high molecular weight polyethylene sheet, Porex Technologies, Fairburn, Ga., U.S.A.). It is derivatized to a specific binding reagent for red blood cells using any suitable means for coupling such reagents to solid supports. In general, the methods for coupling such reagents to the sample zone are identical to those described hereinbelow for affixing labeling reagents to the label zone.

In a preferred embodiment, the sample zone 23 is made of a membrane capable of non-bibulous lateral flow as described previously. The zone is individually backed with a layer of mylar 24. The sample zone is preferably between about 3 and 11 mm wide and between about 5 and 20 mm long and between about 0.1 and 1 mm thick. More preferably the zone is 9 mm wide and 11 mm long and 0.5 mm thick. The mylar is between about 0.01 and 1 mm thick, preferably 0.1 mm thick and has the same width and length dimensions as the sample zone. The mylar portion of the mylar-backed sample zone is affixed to one end of the mylar base sheet 21 as indicated in FIG. 1.

The nitrocellulose section 27 is preferably between about 3 and 11 mm wide and between about 5 and 50 mm long and between about 0.1 and 1 mm thick. More preferably the nitrocellulose section is 9 mm wide and 20 mm long and 0.5 mm thick. The nitrocellulose section is backed with a layer of mylar 30. The mylar is between about 0.01 and 1 mm thick, preferably 0.1 mm thick and has the same width and length dimensions as the nitrocellulose section. The mylar portion of the mylar backed nitrocellulose section is affixed to the mylar base sheet 21 at a distance of between 5 to 20 mm from sample zone 23, preferably 9 mm from the sample zone.

The nitrocellulose section 27 contains a region representing a capture zone 29 (or contains multiple capture zones) that comprises at least one capture reagent capable of appropriate interaction with the label in the form supplied as an index to the amount or presence of analyte. The capture reagent is affixed physically, chemically, biologically or otherwise to the nitrocellulose matrix in a manner such that when labeled moieties are introduced into the zone, they are captured when associated with the appropriate binding partner and allowed to pass through the zone when not so associated. It is not necessary that the capture reagent be bound directly to the matrix; for example, the reagent may be attached to another material which in turn is physically entrapped in the capture zone or otherwise affixed thereto. For example, a reagent may be attached covalently or passively to beads or the like, and the beads then affixed on the membrane. It is important, however, that the capture reagent not be removed from the capture zone when the test device is subjected to whatever treatments are appropriate to remove unbound materials therefrom. Appropriate methods to affix suitable capture agents to the matrix of the capture/detection zone are well known in the art. A preferred method is to affix the appropriate binding partner to a line spotted onto the capture zone.

A label zone 26 is present in some embodiments. In some forms of these embodiments, the label zone 26 is constructed of a matrix or solid support capable of non-bibulous flow such as SONTARA as described previously. The zone is backed with a layer of mylar 25. The label zone is preferably between about 3 and 11 mm wide and between about 5 to 20 mm long and between about 0.1 and 1 mm thick. More preferably the zone is 9 mm wide and 11 mm long and 0.5 mm thick. The mylar is between about 0.01 and 1 mm thick, preferably 0.1 mm thick and has the same width and length dimensions as the label zone. The flow matrix portion of the mylar-backed label zone is affixed to the mylar base sheet such that it fills the gap between the sample zone 23 and the nitrocellulose section 27. The label zone overlaps the sample zone by between about 0.5 and 2 mm and more preferably 1 mm and further overlaps the nitrocellulose section by between about 0.5 and 2 mm and more preferably 1 mm.

A window 15 covers the capture detection zone so that the binding of label can be observed as an indicator of the presence or absence or the amount of analyte. The window is comprised of a thin, clear or translucent material. A top cover 17 is constructed and adapted to fit snugly with the bottom cover 11. The top forms and defines two openings: the sample introduction aperture 35 and the indicator aperture 37. Those openings may have chambered or beveled sides and may be in any shape or size or configuration of convenience. The sample introduction aperture allows for the introduction of the sample into the sample zone 23. The indicator aperture covers window 15 and allows for the reading of the results of the assay contained in capture zone 29. A series of slits 39 in the top cover 17 allows for the evaporation of fluid from absorbent zone 31. The absorbent zone is preferably between about 3 and 11 mm wide and between about 5 and 50 mm long and between about 0.2 and 2 mm thick. More preferably the zone is 9 mm wide and 30 mm long and 0.7 mm thick. The absorbent zone is affixed to the mylar base sheet 21 and overlaps the nitrocellulose section 27 by between about 0.5 and 2 mm and more preferably 1 mm.

Figure 2:
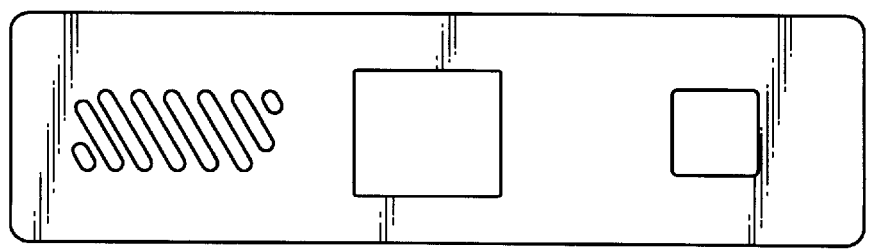
FIG. 2 is a top plan view of the preferred embodiment of the invention.

FIG. 2 is the top plan view of the above described apparatus when assembled.

In operation, the sample zone 23 receives the whole blood sample. The sample zone 23 contains a reagent capable of binding red blood cells, such as antiserum or antibody. The red blood cells are thus retained on the sample pad and the RBC-free fluid remaining flows into the remainder of the device. The label zone 26 if present contains the label to be bound to or designed to compete with analyte in the sample. In an alternate embodiment, the sample zone 23 receives the whole blood sample and the label zone 26 contains both the reagent for capture of the red blood cells and the label as above. In either embodiment, the RBC capture reagent may be an antibody including monoclonal or polyclonal antibodies or immunologically reactive antibody fragments such as F(ab')$_2$, Fab' or Fab or may be a lectin or other RBC-binding agent. The sample zone 23 and label zone 26 are in fluid connection, with the label zone above and slightly overlapping the sample zone such that the fluid will flow from the sample zone to the label zone in the device of FIG. 1. The label zone 26 and the nitrocellulose section 27 are also in fluid connection such that the fluid will flow to capture zone 29. Upon reaching the capture zone 29, the capture reagent designed specifically to bind the desired labeled form removes this labeled moiety from the fluid. The remaining fluid then passes through the capture zone and into the absorbent zone 31.

EXAMPLES

The following examples are intended to illustrate but do not limit the invention.

Example 1

Two different rabbit antisera to human red blood cells (anti-RBC), one prepared in house (BB#31) and another obtained commercially (DAKO A104) were tested. The device shown in FIG. 1 was used. To obtain a solid support for capture of RBCs, cell-free whole serum was dispersed into Sontara™ pads in the presence of 10 mg/ml methylated bovine serum albumin (mBSA). The two different antisera in their respective SONTARA™ pads were then lyophilized for 24 hours.

The resultant antiserum-containing pads were used to prepare test strips as shown in FIG. 1 with the antiserum pad either in the sample zone position, or the label zone position. Controls used sample and label zones that did not contain antiserum. When 40 µl whole blood was added to the sample pad, both antisera prevented the RBCs in the sample from entering the nitrocellulose (see Table I).

TABLE I

| Rabbit anti-RBC Whole Serum | Nitrocellulose Entry |
| --- | --- |
| BB #31 | No |
| DAKO | No |

Example 2

Non-immunized rabbit serum and anti-RBC rabbit serum were lyophilized onto Sontara™ and placed in the sample zone positions of the device shown in FIG. 1. When 40 µl whole blood was applied, the red cells entered the label zone in both cases, however, the extent of migration into the nitrocelluose region was less for the strip prepared with anti-RBC serum and separation of RBCs from plasma was effected (see Table II).

TABLE II

| | Distance Red Cells Migrated Into Nitrocellulose | Plasma Separation From Cells |
| --- | --- | --- |
| Rabbit anti-RBC Serum | 1 mm | Yes |
| Non-immunized Rabbit Serum | 3 mm | No |

Example 3

In an assay for IgE in whole blood, the following protocol was used. Anti-RBC serum was lyophilized into a Sontara™ matrix used as the sample zone and positioned in the device or FIG. 1. Colored particles coupled to monoclonal mouse anti-human IgE antibody were lyophilized into Sontara™ matrix used as the label zone. Polyclonal goat anti-human IgE was applied to the nitrocellulose capture zone.

Whole blood samples were prepared with IgE of 200, 100, 50, 20 and 10 IU/ml using heparinized whole blood from a donor at 10 IU/ml total IgE and another whole serum at 15,000 IU/ml. A dose response was demonstrated for these samples and showed that the assay for total IgE was unaffected by the presence of the whole anti-RBC antiserum (see Table III). Total IgE signal was detected in a heparinized whole blood sample from a second donor. Red cells did not enter the nitrocellulose capture zone of the test strip.

TABLE III

| IqE (IU/ml) | Result |
|---|---|
| 200 | +++ |
| 100 | +++ |
| 50 | ++ |
| 20 | + |
| 10 | +/− |

Example 4

Strips prepared with colored particles in the label zone were used to test blood samples from A-positive, B-positive, and O-positive donors for IgE in order to show that human blood groups respond indistinguishably. With these samples, dispensed at 50 µl volume, red blood cells were prevented from entering the nitrocellulose and a positive Total IgE response was observed (see Table IV).

TABLE IV

| Donor Type | Nitrocellulose Entry | Plasma Separation | IgE* Response |
|---|---|---|---|
| A+ | No | Yes | Yes |
| B+ | No | Yes | Yes |
| O+ | No | Yes | Yes |

(*After spiking whole blood with IgE)

Modifications of the above described modes for carrying out the invention that are obvious to persons of skill in the fields of medicine, immunology, clinical chemistry and/or related field are intended to be within the scope of the following claims:

We claim:

1. A lateral flow device for determining of the presence, absence, or amount of an analyte in a whole blood sample, which device comprises:
   i) a sample receiving zone comprising a first solid porous matrix with an irreversibly immobilized reagent that specifically binds red blood cell surface antigens and effects the removal of substantially all red blood cells (RBCs) from the whole blood sample to result in a substantially RBC-free fluid containing dissolved or dispersed components, said sample receiving zone being in lateral flow contact with
   ii) a labeling zone comprising a second solid porous matrix with a mobilizable labeling component comprising a visible label coupled to a ligand selected from the group consisting of the analyte, a competitive analog of the analyte and a specific binder partner which specifically binds to the analyte and the analog, said labeling zone being in lateral flow contact with
   iii) a capture zone comprising a third solid porous matrix with an immobilized capture reagent, said capture zone being in lateral flow contact with
   iv) an absorbent zone;
wherein said sample receiving zone is separately prepared and positioned contiguous with the remainder of the device prior to application of the sample; wherein the first, the second and third solid porous matrices are non-bibulous matrices; and wherein all of said dissolved or dispersed components in said RBC-free fluid flow through the sample receiving zone, labeling zone and capture zone in a non-bibulous flow.

2. The device of claim 1 wherein the labeling component comprises the visible label coupled to the specific binding partner for said analyte.

3. The device of claim 1 wherein the labeling component comprises the visible label coupled to the competitive analog of the analyte.

4. The device of claim 1 wherein the first solid porous matrix is selected from the group consisting of paper, nitrocellulose, and nylon and wherein said matrix is converted to a non-bibulous material through the application of an effective concentration of methylated bovine serum albumin, and then the reagent that specifically binds red blood cell surface antigens is immobilized on said matrix, and said matrix is then lyophilized to provide for irreversible immobilization of the reagent.

5. The device of claim 1 wherein the reagent that specifically binds red blood cell surface antigens is selected from the group consisting of monoclonal antibody, polyclonal antibodies, and their $F(ab')_2$, Fab' and Fab fragments.

6. The device of claim 1 in which said first solid porous matrix, second solid porous matrix and third solid porous matrix each further comprise a non-woven fabric structure.

7. The device of claim 6 wherein said fabric has a spunlaced structure.

8. The device of claim 1 wherein said first solid porous matrix, second solid porous matrix and third solid porous matrix further each are comprised of a high density polyethylene sheet.

9. The device of claim 8, wherein said sheet has an open pore structure with a density, at 40% void volume, of 0.57 gm/cc and an average pore diameter of 1 to 250 micrometers.

10. The device of claim 1 wherein said zones have a pore size of about 1–100 micrometers.

11. A method to determine the presence, absence, or amount of analyte in a whole blood sample which method comprises the steps of:
   (a) contacting the whole blood sample with the device of claim 1; and
   (b) visually observing the binding of the labeling component in the third solid porous matrix as a function of the presence or absence or amount of the analyte in the whole blood sample.

* * * * *